US006479302B1

(12) United States Patent
Dremel

(10) Patent No.: US 6,479,302 B1
(45) Date of Patent: Nov. 12, 2002

(54) METHOD FOR THE IMMUNOLOGICAL DETERMINATION OF AN ANALYTE

(75) Inventor: Bernd Dremel, Darmstadt (DE)

(73) Assignee: Merck Patent Gesellschaft MIT, Darmstadt (DE)

( * ) Notice: Subject to any disclaimer, the term of this patent is extended or adjusted under 35 U.S.C. 154(b) by 0 days.

(21) Appl. No.: 09/355,555

(22) PCT Filed: Jan. 30, 1997

(86) PCT No.: PCT/EP97/00403

§ 371 (c)(1),
(2), (4) Date: Nov. 17, 1999

(87) PCT Pub. No.: WO98/34114

PCT Pub. Date: Aug. 6, 1998

(51) Int. Cl.$^7$ ............................................. G01N 33/553
(52) U.S. Cl. ...................... 436/526; 436/517; 436/518; 436/523; 436/527; 436/528; 436/529; 436/530; 436/531; 436/532; 436/533; 436/535; 436/538; 436/548; 436/806; 436/805; 435/2; 435/4; 435/7.1; 435/7.92; 435/7.93; 435/7.94; 435/7.95; 435/971; 435/970
(58) Field of Search .................................. 436/517, 518, 436/523, 526, 527, 528, 529, 530, 531, 532, 533, 535, 538, 548, 805, 806; 435/2, 4, 7.1, 7.92–7.95, 971, 970

(56) References Cited

U.S. PATENT DOCUMENTS

| | | | | | |
|---|---|---|---|---|---|
| 3,985,649 | A | * | 10/1976 | Eddelman | 210/42 |
| 4,115,534 | A | * | 9/1978 | Ithakissios | 424/1 |
| 4,169,804 | A | * | 10/1979 | Yapel, Jr. | 252/62.53 |
| 4,272,510 | A | * | 6/1981 | Smith et al. | 427/47 |
| 4,628,037 | A | * | 12/1986 | Chagnon et al. | 436/526 |
| 4,695,393 | A | * | 9/1987 | Whitehead et al. | 252/62.54 |
| 4,698,302 | A | * | 10/1987 | Whitehead et al. | 435/94 |
| 4,978,610 | A | * | 12/1990 | Forrest et al. | 435/7 |
| 5,076,950 | A | * | 12/1991 | Ullman et al. | 252/62.51 |
| 5,252,459 | A | * | 10/1993 | Tarcha et al. | 435/6 |
| 5,270,169 | A | * | 12/1993 | Chang et al. | 435/7.24 |
| 5,374,531 | A | * | 12/1994 | Jensen | 435/7.24 |
| 5,385,822 | A | * | 1/1995 | Melnicoff et al. | 435/5 |
| 5,387,893 | A | * | 2/1995 | Oguriyama et al. | 335/302 |
| 5,445,971 | A | * | 8/1995 | Rohr | 436/526 |
| 5,558,839 | A | * | 9/1996 | Matte et al. | 422/101 |
| 5,567,326 | A | * | 10/1996 | Ekenberg et al. | 210/695 |
| 5,602,042 | A | * | 2/1997 | Farber | 436/526 |
| 5,705,402 | A | * | 1/1998 | Leland et al. | 436/526 |
| 5,776,784 | A | * | 7/1998 | Kegelman et al. | 436/526 |
| 5,942,124 | A | * | 8/1999 | Tuunanen | 210/695 |
| 5,968,839 | A | * | 10/1999 | Blatt et al. | 436/513 |
| 5,994,145 | A | * | 11/1999 | Stave et al. | 436/139 |
| 6,020,211 | A | * | 2/2000 | Tuunanen | 436/526 |
| 6,040,192 | A | * | 3/2000 | Tuunanen | 436/177 |
| 6,065,605 | A | * | 5/2000 | Korpela et al. | 209/216 |
| 6,136,549 | A | * | 10/2000 | Feistel | 435/7.1 |
| 6,197,597 | B1 | * | 3/2001 | Tuunanen | 436/518 |
| 6,207,463 | B1 | * | 3/2001 | Tuunanen | 436/526 |

* cited by examiner

Primary Examiner—Christopher L. Chin
Assistant Examiner—Pensee T. Do
(74) Attorney, Agent, or Firm—Millen, White, Zelano & Branigan, P.C.

(57) ABSTRACT

The invention concerns a method for the immunological determination of an analyte in a sample using magnetic particles coated with the analyte to be determined or analyte-specific bonding partners and directly detectable non-magnetic particles coated with analyte-specific bonding partners or the analyte to be determined or using a non-magnetic substance which is indirectly detectable, and incubation of the reaction mixture. The method is characterized in that the magnetic particles are subsequently separated from the reaction mixture using a magnetic test strip and the analyte concentration is determined directly.

18 Claims, No Drawings

METHOD FOR THE IMMUNOLOGICAL DETERMINATION OF AN ANALYTE

The invention relates to a procedure for the immunological determination of an analyte in a sample solution with the aid of magnetic and non-magnetic particles.

Immunological methods for the determination of analytes with magnetic and non-magnetic particles are disclosed, for example, in WO 95/04279. In these methods, the magnetic particles are precipitated in the reaction solution by a magnetic field after the incubation; the analyte is then photometrically determined in the supernatant. JP 05-52849 describes a chromatographic system which is provided with a magnet. The capillary medium here fulfils the task of a filter. The driving force which forces the analyte through the filter or the capillary is the magnetic force.

The known procedures have a number of disadvantages. The magnetic separation of the particles by precipitation in the reaction solution has the disadvantage that a direct photometric, fluorimetric or electrochemical detection of the analyte is not possible without further washing or separation steps. A deficiency of the filtration systems is that the filters or capillaries easily block, viscosity problems occur and the analyte is adsorbed prematurely on the chromatographic material, i.e. before the binding reaction, so that only selected sample material can be reliably analysed.

The present invention is based on the object of avoiding the disadvantages outlined in immunological procedures which operate using magnetic particles, and of making available a very simple and reliable procedure.

The present invention relates to a procedure for the immunological determination of an analyte in a sample with the aid of magnetic particles coated with the analyte to be determined or analyte-specific binding components and directly detectable non-magnetic particles coated with analyte-specific binding components or the analyte to be determined, or of an indirectly detectable non-magnetic substance and incubation of the reaction mixture, which is characterized in that the magnetic particles are then removed from the reaction mixture using a magnetic test strip and the analyte concentration is determined directly.

Preferably, the analyte concentration is determined directly on the magnetic test strip visually or reflectometrically. The determination can also be carried out indirectly by development of a colour reaction or electrochemically on the test strip.

Analyte is especially understood as meaning the diagnostically relevant constituents of body fluids, i.e. haptens or antigens; analyte-specific binding components are understood as meaning monoclonal and polyclonal antibodies.

The magnetic test strips according to the invention can be prepared, for example, from suitable magnetizable pigments similarly to diskettes, audio or video tapes. Very flat permanent magnets are preferably suitable. The use of rare earth metal alloys allows the production of permanent magnets having particularly high residual magnetism. In the simplest case, it is possible to use for the procedure according to the invention a flat permanent magnet which is completely covered with white, smooth card and is sealed with plastic adhesive strips on the edges. The magnetic test strip can be used a number of times by wiping off the magnetic particles from the smooth surface after carrying out the test.

A great advantage of the magnetic strip technology in comparison with the direct conventional coupling of antibodies to the surface of test strips is to be regarded in that the reaction with the analyte initially proceeds homogeneously or quasi-homogeneously. Diffusion problems, which restrict the lower detection range in heterogeneous reactions between test strips and analytes, play virtually no part in the homogeneous medium.

Conversely, in heterogeneous reactions which are often diffusion-limited, various measures are undertaken to improve the substance exchange between reaction surface and analyte solution (filtration of the analyte through the test strip surface). The advantages achievable by these measures, however, cannot compensate for the advantage of the quasi-homogeneous reaction between analyte and small suspended particles with a high surface area (problems as a result of pore diffusion, clogging effects).

Particles which can be used in principle are all commercially obtainable magnetic and non-magnetic particles, which can also be coloured, provided they have a size from 30 nm to 800 m. Suitable particles are inorganic and organic particles, e.g. magnetic particles of iron, nickel, cobalt, manganese, elements of the lanthanide series such as neodymium, erbium etc., particles of magnetic alloys such as aluminium, nickel, cobalt and copper alloys, oxides such as $Fe_3O_4$, $CrO_2$, $CoO$, $NiO_2$, $Mn_2O_3$ etc., composite materials such as ferrites and organic polymers such as polystyrene.

The procedure according to the invention is especially suitable for the detection of analytes for which specific binding component exists. Implementation takes place, for example, by the known sandwich immunoassay or competitive immunoassay procedures. After the incubation, the magnetic particles are removed with the aid of the magnetic test strip such that the directly detectable non-magnetic particles and the indirectly detectable non-magnetic substance remain in the reaction mixture, provided they are not bound to the magnetic particles. Detection is carried out visually on the surface of the test strip either directly, e.g. by the presence or absence of differently coloured non-magnetic particles, or indirectly, e.g. when the non-magnetic substance is an enzyme, by the development of a colour reaction on the test strip. If the non-magnetic substance is an enzyme, the detection can also be carried out electrochemically on the magnetic test strip. The test strip is then a magnetic electrode.

The direct immunological determination of an analyte with coloured non-magnetic particles by the sandwich method is carried out, for example, in such a way that a monoreagent is incubated with the sample solution. The monoreagent consists of magnetic particles which are coated with analyte-specific, preferably monoclonal antibodies and differently coloured non-magnetic particles, which are also coated with preferably monoclonal antibodies, these antibodies being directed against another epitope of the analyte. The particles are suspended in a suitable buffer solution. If the analyte is present in the sample solution, the differently coloured non-magnetic particles can bind to the magnetic particles. After passage of an adequate reaction time, the magnetic particles are removed from the reaction mixture using a magnetic test strip. The magnetic particles bound to the surface of the test strip are directly evaluated visually by means of a colour scale or using a reflectometer. The colour change on the test strip depends directly on the number of the bound non-magnetic differently coloured particles and is proportional to the analyte concentration. Two wavelength measurements can moreover compensate for inhomogeneities in the attachment of the magnetic particles to the test strip.

The immunological determination by the competitive assay method is carried out, for example, with a bireagent.

Reagent 1 contains magnetic particles which are coated with analyte-specific (monoclonal or polyclonal) antibodies, in a suitable buffer solution. Reagent 2 contains differently coloured non-magnetic particles, which are coated with the analyte to be determined, in the same buffer solution. The sample solution is initially incubated with the reagent 1. If the analyte is present in the sample solution, binding sites of the analyte-specific antibodies on the magnetic particles are saturated according to the concentration of the analyte in the sample. After a suitable incubation time, the reagent 2 is added to the reaction mixture. The differently coloured non-magnetic particles coated with the analyte can bind to the magnetic particles, provided the binding sites of the antibodies are not already blocked by the analyte. After passage of a certain reaction time, the magnetic particles are removed from the reaction mixture using the magnetic test strip according to the invention. The magnetic particles bound to the surface of the test strip are directly evaluated visually by means of a colour scale or using a reflectometer. The colour change on the test strip depends directly on the number of the bound non-magnetic differently coloured particles and is inversely proportional to the analyte concentration. Two wavelength measurements can moreover compensate for inhomogeneities in the attachment of the magnetic particles to the test strip. The bireagent can also be composed such that the magnetic particles are coated with the analyte, and the non-magnetic particles with the antibody; the detection principle is unchanged.

An indirect immunological determination of an analyte with a non-magnetic substance, e.g. an enzyme, by the sandwich method can be carried out as follows. A monoreagent which contains magnetic particles which are coated with an analyte-specific, preferably monoclonal antibody, in a buffer solution, and a non-magnetic substance, preferably an enzyme, which is coupled to preferably monoclonal antibodies, but contains an antibody which is directed against an epitope of the analyte other than the antibodies on the magnetic particles, is incubated with the sample solution. If analyte is present in the sample, the non-magnetic substance binds to the magnetic particles. After passage of a certain reaction time, the magnetic particles are removed from the reaction mixture using a magnetic test strip. A chemical reaction for the detection of the non-magnetic substance is then carried out on the test strip. If the non-magnetic substance is an enzyme, it is possible, for example, for a leuco dye immobilized on the test strip to be converted enzymatically into a dye. The colour change on the test strip can be directly evaluated visually by means of a colour scale or using a reflectometer. It is proportional to the analyte concentration.

Suitable buffer solutions are those which are able to maintain a pH range of 5 to 9, such as phosphate buffer, tris, borate, HEPES and PIPES buffer etc.

EXAMPLE 1

Determination of Cortisol by the Competitive Assay

Reagent 1: 50 mM phosphate buffer solution containing suspended magnetic particles which are coated with anti-cortisol antibodies.

Reagent 2: 50 mM phosphate buffer solution containing cortisol coupled to alkaline phosphatase.

30 $\mu$l of sample solution (serum) are preincubated with 150 $\mu$l of reagent 1 for 3 minutes and then incubated for a further 3 minutes with 150 $\mu$l of reagent 2. By means of brief immersion of the magnetic test strip in the reaction solution (1 minute), the suspended magnetic particles are bound to the surface of the test strip. The test strip is then immersed for 1 minute in the substrate solution (para-nitrophenyl phosphate solution). After a reaction time of about 5 minutes, the analyte concentration is determined qualitatively by colour comparison with a reference test strip.

In the reaction, a displacement competition occurs between the total cortisol of the serum and the cortisol labelled with alkaline phosphatase. The amount of labelled cortisol which is bound to the particles is all the higher, the lower the amount of total cortisol in the serum. The colour change on the test strip is inversely proportional to the analyte concentration.

EXAMPLE 2

Determination of Ferritin

Reagent 1: 0.2 M tris buffer solution containing suspended magnetic particles which are coated with anti-ferritin antibodies.

Reagent 2: 0.2 M tris buffer solution containing ferritin coupled to alkaline phosphatase.

The determination is carried out analogously to Example 1 using paranitrophenyl phosphate as substrate solution. After a reaction time of 4 minutes, the ferritin concentration is determined qualitatively by colour comparison of the magnetic test strip with reference test strips.

EXAMPLE 3

Determination of TNT in Water Samples

The TNT reagent consists of a 50 mM phosphate buffer solution of pH 7.4 containing suspended magnetic particles (100 $\mu$g/ml) which are coated with anti-TNT antibodies (IgG1, lot: 103726 from SDI) (reagent 1), and a buffered competition solution (TNT-alkaline phosphatase conjugate, lot: 103881, SDI, diluted 1:80 in 50 mM TRIS buffer, pH 8.0, 0.15 M NaCl, 1 MM $MgCl_2$. 6 $H_2O$, 0.1 mM $ZnCl_2$, 2.5% BSA, 5% sucrose, 0.1% $NaN_3$ (reagent 2).

100 $\mu$l of sample (TNT solution in 40 mM HEPES buffer are preincubated with 150 $\mu$l of reagent 1 for 2 minutes and then incubated for a further 2 minutes with 150 $\mu$l of reagent 2. By immersion of the magnetic test strip in the reaction solution (1 minute), the suspended magnetic particles are bound to the surface of the test strip. The test strip is then immersed for 1 minute in a substrate solution (para-nitrophenyl sulphate solution). After a further 4 minutes reaction time, the analyte concentration is determined qualitatively by colour comparison with the reference test strip. The total analysis time is about 10 minutes.

In the reaction, a displacement competition occurs between the TNT of the water sample and the AP-labelled TNT. The amount of labelled TNT which is bound to the particles is all the higher, the lower the TNT content of the water sample. After the reaction, the magnetic particles are bound to the test strip and incubated in the substrate solution. The colour change on the test strip is inversely proportional to the analyte concentration.

What is claimed is:

1. A procedure for the immunological determination of an analyte in a sample comprising
   a) incubating a sample which may comprise said analyte with
   i) magnetic particles coated with a) the analyte to be determined or b) a first analyte-specific binding components and either ii) directly or indirectly detectable non-magnetic particles coated with a) a second analyte-specific binding component or b) the analyte to be determined, or iii) an indirectly detectable non-magnetic substance coupled to said second analyte-specific binding component;

b) allowing said analyte and said coated magnetic particles and either said coated non-magnetic particles or said coupled non-magnetic substance to interact;

c) removing said magnetic particles and materials attached thereto by inserting and removing a magnetic test strip; and d) determining the analyte concentration directly on said removed magnetic test strip.

2. A procedure for the imunological determination of an analyte in a sample comprising a) incubating a sample which may comprise said analyte with i) magnetic particles coated with a) the analyte to be determined or b) a first analyte-specific binding components and either ii) directly or indirectly detectable non-magnetic particles coated with a) a second analyte-specific binding component or b) the analyte to be determined, or iii) an indirectly detectable non-magnetic substance coupled to said second analyte-specific binding component;

b) allowing said analyte and said coated magnetic particles and either said coated non-magnetic particles or said coupled non-magnetic substance to interact;

c) removing said magnetic particles and materials attached thereto by inserting and removing a magnetic test strip; and d) determining the analyte concentration indirectly by development of a color reaction or electrochemically on said removed test strip.

3. The method according to claim 1, wherein said two analyte-specific binding components are antibodies.

4. The method according to claim 3, wherein said two antibodies are monoclonal antibodies which are specific for different epitopes of said analyte.

5. The method according to claim 1, wherein said non-magnetic substance is an enzyme.

6. The method according to claim 1, wherein the magnetic test strip is a flat permanent magnet.

7. The method according to claim 1, wherein the magnetic test strip can be washed and reused a plurality of times.

8. The method according to claim 1, wherein said particles have a size of 30 nm to 800 µm.

9. The method according to claim 1, wherein said particles are of iron, nickel, cobalt, manganese, a lanthanide, a magnetic alloy, an oxide, a composite material, or an organic polymer.

10. The method according to claim 9, wherein said lanthanide is neodymium or erbium, said magnetic alloy is an aluminum, nickel, cobalt or copper alloy, said oxide is $Fe_3O_4$, $CrO_2$, $CoO$, $NiO_2$ or $Mn_2O_3$, said composite material is a ferrite, or said organic polymer is a polystyrene.

11. A procedure for the immunological determination of an analyte in a sample, comprising a) incubating a sample which may comprise said analyte with (i) magnetic particles coated with a first analyte-specific binding component and (ii) non-magnetic particles, optionally having a color different from said magnetic particles, coated with a second analyte-specific binding component, wherein said coated non-magnetic particles are directly or indirectly detectable;

b) allowing said analyte and said coated magnetic particles and said coated non-magnetic particles to interact;

c) removing said magnetic particles and materials attached thereto by inserting and removing a magnetic test strip; and d) determining the analyte concentration.

12. The method according to claim 11, wherein said first and second analyte-specific binding components are monoclonal antibodies.

13. A procedure for the immunological determination of an analyte in a sample comprising magnetic particles coated with an analyte-specific component, to which the analyte and directly or indirectly detectable non-magnetic materials are attached, comprising removing said magnetic particles and said directly or indirectly detectable materials attached thereto from said sample by inserting a magnetic test strip into the sample and removing it, and determining the analyte concentration directly on said removed test strip.

14. The method according to claim 13, wherein said analyte-specific binding component is a monoclonal antibody.

15. A procedure for the immunological determination of an analyte in a sample comprising a) incubating a sample which may comprise said analyte with (i) magnetic particles coated with said analyte or with a first analyte-specific component; and (ii) non-magnetic particles, optionally having a different color from said magnetic particles, coated with a second analyte-specific binding component or with said analyte;

b) allowing said analyte and said coated magnetic particles and said coated non-magnetic particles to interact;

c) removing said magnetic particles and materials attached thereto by inserting and removing a magnetic test strip; and d) determining the analyte concentration directly on said removed magnetic test strip.

16. The method according to claim 15, wherein said analyte-specific binding components are monoclonal antibodies.

17. A procedure for the immunological determination of an analyte in a sample, comprising a) incubating a sample which may comprise said analyte with (i) magnetic particles coated with a first analyte-specific binding component and (ii) an indirectly detectable non-magnetic substance, coupled to a second analyte-specific binding component, b) allowing said analyte and said coated magnetic particle and said non-magnetic substance to interact;

c) removing said magnetic particles and materials attached thereto by inserting and removing a magnetic test strip; and d) determining the analyte concentration directly on said removed magnetic test strip.

18. The method according to claim 17, wherein said analyte-specific binding components are monoclonal antibodies.

* * * * *

UNITED STATES PATENT AND TRADEMARK OFFICE
CERTIFICATE OF CORRECTION

PATENT NO.   : 6,479,302 B1               Page 1 of 1
DATED        : November 12, 2002
INVENTOR(S)  : Dremel It is certified that error appears in the above-identified patent and that said Letters Patent is hereby corrected as shown below:

<u>Title page, Item [54] and Column 1, line 1,</u>
Change "METHOD" to -- PROCEDURE --.

Signed and Sealed this

Nineteenth Day of August, 2003

JAMES E. ROGAN
*Director of the United States Patent and Trademark Office*